(12) United States Patent
Klein et al.

(10) Patent No.: US 9,234,262 B2
(45) Date of Patent: Jan. 12, 2016

(54) PALLADIUM-BASED ALLOYS FOR USE IN THE BODY AND SUITABLE FOR MRI IMAGING

(75) Inventors: Arthur S. Klein, Orange, CT (US); Edward F. Smith, III, Madison, CT (US); Peter Hale, Windsor, CT (US)

(73) Assignee: DERINGER-NEY, INC., Bloomfield, CT (US)

( * ) Notice: Subject to any disclaimer, the term of this patent is extended or adjusted under 35 U.S.C. 154(b) by 1321 days.

(21) Appl. No.: 12/358,629

(22) Filed: Jan. 23, 2009

(65) Prior Publication Data

US 2009/0191087 A1 Jul. 30, 2009

Related U.S. Application Data

(60) Provisional application No. 61/024,106, filed on Jan. 28, 2008.

(51) Int. Cl.
*C22C 5/04* (2006.01)
*A61N 1/08* (2006.01)

(52) U.S. Cl.
CPC ............. *C22C 5/04* (2013.01); *A61N 2001/086* (2013.01)

(58) Field of Classification Search
CPC ........................................................ C22C 5/04
USPC ................... 148/430; 420/463–465
See application file for complete search history.

(56) References Cited

U.S. PATENT DOCUMENTS

| 4,412,970 A * | 11/1983 | Prasad ........................ 420/463 |
| 4,681,735 A * | 7/1987 | Groll et al. .................. 420/464 |
| 4,836,984 A * | 6/1989 | Wagner et al. ............... 420/464 |
| 5,139,891 A * | 8/1992 | Cowie et al. ................. 428/670 |
| 5,298,218 A * | 3/1994 | Groll et al. .................. 420/463 |
| 6,585,755 B2 | 7/2003 | Jackson et al. |
| 6,849,231 B2 | 2/2005 | Kojima et al. |
| 6,982,059 B2 | 1/2006 | Liang et al. |
| 7,087,077 B1 * | 8/2006 | Van Dijk et al. ............. 623/1.15 |
| 7,128,757 B2 | 10/2006 | Boylan et al. |
| 2004/0153138 A1 | 8/2004 | Murphy |

(Continued)

FOREIGN PATENT DOCUMENTS

DE 32 11 703 A1 10/1983
DE 34 47 413 A1 6/1986

(Continued)

OTHER PUBLICATIONS

Spencer, J.F. et al. "The magnetic susceptibility of some binary alloys", Proceedings of the Royal Society of London, Series A, containing papers of a mathematical and physical character, vol. 115, No. 773, pp. 61-73 (1927).

(Continued)

*Primary Examiner* — Brian Walck
(74) *Attorney, Agent, or Firm* — Bridget M. Hayden; Dorsey & Whitney LLP

(57) ABSTRACT

Ultra-low magnetic susceptibility, biocompatible palladium-tin, palladium-aluminum, and palladium-tantalum alloys include at least 75 at % palladium, between about 3 and 20 at % tin, aluminum, or tantalum, respectively, and one or more other additives chosen from niobium, tungsten, molybdenum, zirconium, titanium, tin for non-palladium-tin alloys, aluminum for non-palladium-aluminum alloys, or tantalum for non-palladium-tantalum alloys, up to about 22 at % total.

26 Claims, 5 Drawing Sheets

(56) References Cited

U.S. PATENT DOCUMENTS

| | | | |
|---|---|---|---|
| 2005/0070793 | A1 | 3/2005 | Pacetti et al. |
| 2005/0121120 | A1 | 6/2005 | Van Dijk et al. |
| 2005/0222656 | A1 | 10/2005 | Wahlstrand et al. |
| 2005/0222657 | A1 | 10/2005 | Wahlstrand et al. |
| 2006/0247748 | A1 | 11/2006 | Wahlstrand et al. |
| 2007/0162108 | A1* | 7/2007 | Carlson et al. ............... 623/1.34 |
| 2007/0280850 | A1 | 12/2007 | Carlson |
| 2008/0049376 | A1 | 2/2008 | Stevenson et al. |
| 2008/0188924 | A1 | 8/2008 | Prabhu |
| 2008/0195194 | A1 | 8/2008 | Pacetti et al. |
| 2012/0039744 | A1 | 2/2012 | Hale et al. |

FOREIGN PATENT DOCUMENTS

| | | |
|---|---|---|
| DE | 10033445 | 1/2002 |
| JP | 09184033 A | 7/1997 |
| WO | WO 2007/070544 A | 6/2007 |

OTHER PUBLICATIONS

Harris, I.R. et al. "A study of some palladium-tin, silver-tin and palladium-silver-tin alloys," *Journal of the Less Common Metals*, Elsevier-Sequoia S.A. Lausanne, CH, vol. 16, No. 3, Nov. 1, 1968, pp. 223-232. (XP024071078, ISSN: 0022-5088).

Schenck, J.F. "The role of magnetic susceptibility in magnetic resonance imaging: MRI magnetic compatibility of the first and second kinds," *Medical Physics*, AIP, Melville, NY, US, vol. 23, No. 6, Jun. 1, 1996, p. 815-850. (XP000597979, ISSN: 0094-2405).

Trampert et al., English machine translation of DE1003345, Jan. 24, 2002, p. 1-6.

Wright, Roger N. "9.5 Projecting Workability From Mechanical Tests", appears in "Chapter 9: Workability in Extrusion and Wire Drawing" of *Workability Testing Techniques*, Dieter, George E. ed., American Society for Metals 1984 pp. 262-268.

* cited by examiner

Schematic of Sample (outside magnetic field)

Pt-8W (current commercial benchmark)

Alloy 1359, Pd-25Al

PALLADIUM-BASED ALLOYS FOR USE IN THE BODY AND SUITABLE FOR MRI IMAGING

CROSS-REFERENCE TO RELATED APPLICATIONS

This application claims priority to U.S. provisional patent application Ser. No. 61/024,106, filed Jan. 28, 2008, and entitled Palladium-Based Alloys for Use in the Body and Suitable for MRI Imaging, which is incorporated by reference herein in its entirety.

FIELD OF THE INVENTION

The present invention relates to MRI compatible materials used to fabricate medical devices and/or aids. In particular, the invention relates to palladium-based alloys having an ultra-low magnetic susceptibility and their use as devices and/or aids compatible for use in MRI settings.

BACKGROUND

Magnetic Resonance Imaging (MRI) compatibility has become an important feature for medical devices as the use of MRI increases and becomes more commonplace. Over the past three decades, MRI has become a valuable medical tool due to its offer of better soft tissue contrast and tissue chemistry, which are not currently obtainable with standard x-ray fluoroscopic imaging, spiral CT scanning and/or ultrasound. With increased computing power and higher strength magnetic fields, today's MRI equipment provides better signal to noise ratios (SNR) and offers the medical community more detailed imaging capabilities. In the mid-1990's, most clinical MRI equipment was based on a 0.5 Tesla field. By increasing field strength to 1.5 T, and then to 3.0 T, the SNR and image quality has improved without inconvenience to the patient or physician. As a result, MRI imaging has become more common in the neurology and internal medicine fields.

The MRI technique utilizes intense magnetic fields. Nonetheless, some biocompatible devices are constructed from metals or metal alloys that are not MRI compatible. MRI incompatibility arises from an interaction with the magnetic field, resulting in a physical force and/or heating of the metal, and/or distortion of the magnetic resonance (MR) image. These incompatibilities may be life threatening. An extreme example would be the reaction of the MRI magnetic field with a ferromagnetic implant, causing the implant to be dislodged from the therapeutic tissue location, resulting in injury, or death. A no less life threatening example of incompatibility would be the malfunctions of a cardiac rhythm device due to incompatible part(s). Alternatively, an incompatible material may have no noticeable physical reaction, typical of many paramagnetic and diamagnetic materials, but may cause image distortion (e.g. image ghosting, image artifact). The image artifact, or "ghost," can be considered an obstruction, and may limit the capability of the MRI to image the surrounding area and thereby reduce the physician's ability to examine critical features. These, so called ghost image effects, can be greater than ten times the size of the object causing the distortion. The less a metal interacts with a magnetic field, the more compatible it will be for an MRI application. In general a material that is not compatible due to magnetic force will not be compatible for image clarity. The field of research shows that device heating of metals in an MRI is largely due to device geometry. Also there are indications that a material's electrical properties may impact image distortion. To complicate the matter further, not all MRI compatible metals or metal alloys are biocompatible, in that the implant or medical device causes an adverse bodily or localized reaction in use.

Some have sought to improve the MRI compatibility of the materials used to construct devices, including the improvement of the MRI compatibility of palladium based metal alloys. In U.S. Pat. No. 7,087,077, filed Mar. 27, 2002, and entitled Biomedical Aid or Implant; and U.S. Patent Application Publication No. 2005/0121120, filed Jan. 14, 2005, and entitled Biomedical Aid or Implant ("the '120 publication"), the use of specific ratios of palladium, gold, and platinum is disclosed, along with additional dopants to improve the alloys imaging characteristics in an MRI. U.S. Patent Application Publication No. 2007/0280850, filed Sep. 23, 2005, and entitled MRI Compatible Devices ("the '850 publication"), discloses a generic combination of "precious" metals and "refractory" metals, to achieve particular properties, such that the magnetic susceptibility of the metal or alloy is greater than, or less than, the magnetic susceptibility of the base metal. The reference sets an upper bound of $3 \times 10^{-4}$ (cgs), volumetric magnetic susceptibility, which is nearly five times greater than pure palladium's magnetic susceptibility of $6.1 \times 10^{-5}$. U.S. Patent Application Publication No. 2007/0162108, filed Dec. 13, 2003, and entitled Implantable Medical Device Using Palladium ("the '108 publication"), provides a similar list of alloying elements. Additionally, U.S. Pat. No. 7,128,757, issued Oct. 31, 2006, and entitled Radiopaque and MRI Compatible Nitinol Alloys for Medical Devices ("the '757 patent"), discloses alloys containing palladium, but seeks to "maintain" the MRI compatibility of the alloy. For example, the susceptibility of Nitinol is listed as $1.9 \times 10^{-5}$, and the susceptibility of a Ni—Ti—Pt alloy is provided as $1.33 \times 10^{-5}$.

In view of the aforementioned references, although some have addressed the general issue of MRI compatibility of medical aids and implants in mechanical, geometrical, or electrical device applications using generic materials, none have dealt with technology needed to formulate alloys with ultra-low magnetic susceptibilities. Accordingly, there is a need for biocompatible medical devices or aids that are MRI compatible, which have an ultra-low magnetic susceptibility.

SUMMARY

Palladium-aluminum, palladium-tantalum and palladium-tin based alloys and/or devices are provided, which have small MRI artifacts, and ultra-low magnetic susceptibilities, making the material and/or device compatible with high magnetic field MRI equipment.

In certain embodiments, a palladium-tin alloy includes at least 75 at % palladium; between about 3 and 20 at % tin; and one or more additives chosen from aluminum, tantalum, niobium, tungsten, molybdenum, zirconium, and titanium, up to about 22 at % total, and is an ultra-low magnetic susceptibility, biocompatible alloy.

In another embodiment, a palladium-aluminum alloy includes at least 75 at % palladium; between about 3 and 20 at % aluminum; and one or more additives chosen from tin, tantalum, niobium, tungsten, molybdenum, zirconium, and titanium, up to 22 at % total, and is an ultra-low magnetic susceptibility, biocompatible alloy.

In a further embodiment, a palladium-tantalum alloy includes least 75 at % palladium; between 3 and 20 at % tantalum; and one or more additives chosen from tin, aluminum, niobium, tungsten, molybdenum, zirconium, and titanium, up to 22 at % total, and is an ultra-low magnetic susceptibility, biocompatible alloy.

In yet another embodiment, a palladium alloy includes at least 75 at % palladium; and at least one of tin, aluminum, and tantalum totaling between about 3 and 25 at %, and is an ultra-low magnetic susceptibility, biocompatible alloy.

In one other embodiment, an electrically active medical device includes a palladium alloy, and the palladium alloy includes at least 75 at % palladium; and at least two of tin, aluminum, tantalum, niobium, tungsten, molybdenum, zirconium and titanium totaling between about 3 and 25 at %, where the portion of the electrically active medical device formed of the palladium alloy has an ultra-low magnetic susceptibility and is biocompatible.

In another embodiment, an electrically passive medical device includes a palladium alloy, and the palladium alloy includes at least 75 at % palladium; and at least two of tin, aluminum, tantalum, niobium, tungsten, molybdenum, zirconium and titanium totaling between about 3 and 25 at %, where the portion of the electrically passive medical device formed of the palladium alloy has an ultra-low magnetic susceptibility and is biocompatible.

These and other features and advantages of aspects of the present invention will become apparent to those skilled in the art from the following detailed description, where it is shown and described in illustrative embodiments, including best modes contemplated for carrying out the invention. As it will be realized, the various aspects of the invention are capable of modifications in various obvious respects, all without departing from the spirit and scope of the present invention. Accordingly, the drawings and detailed description are to be regarded as illustrative in nature and not restrictive.

DETAILED DESCRIPTION

Figure 1:
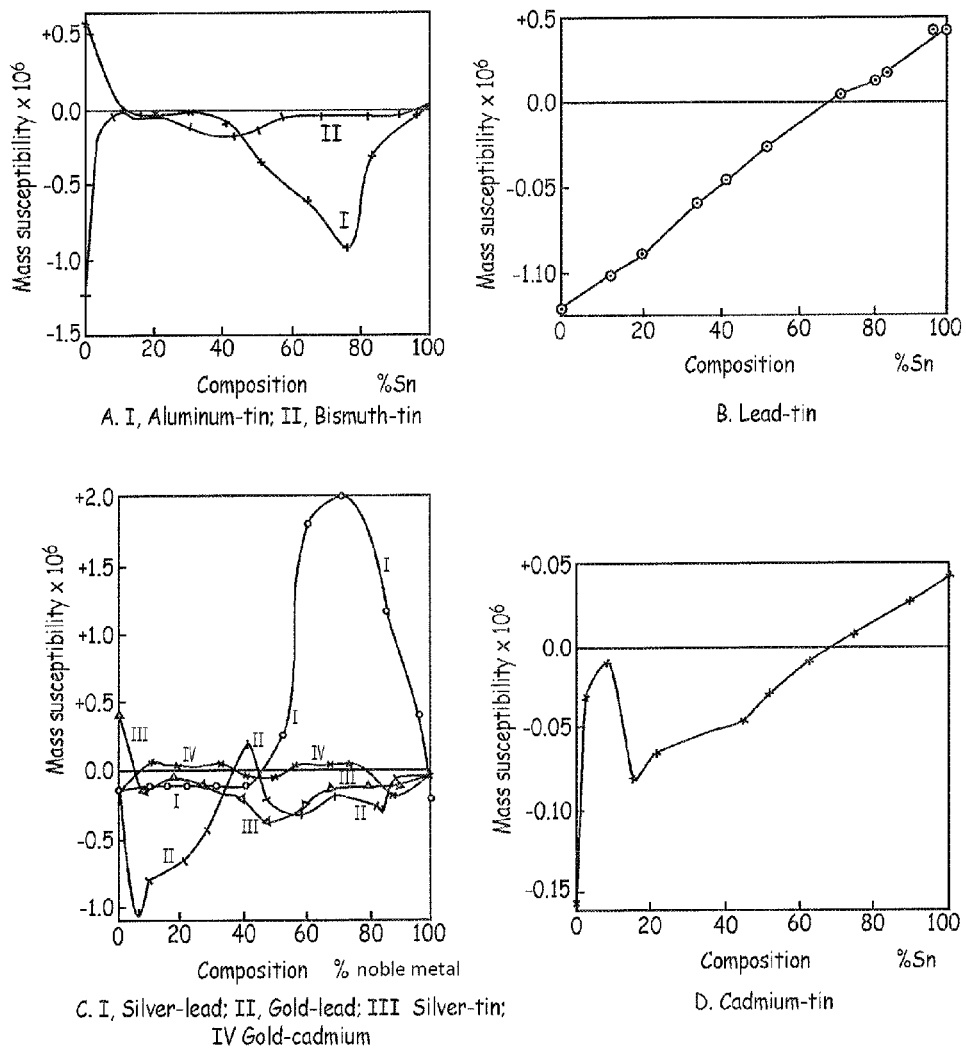
FIG. 1 depicts graphs of magnetic susceptibility (mass) versus composition for binary alloys (A-D) illustrating the unpredictability of magnetic susceptibilities for alloy compositions.

Embodiments of the invention provide combinations of elements for providing an alloy with improved MR imaging performance over known alloys. The embodiments described below use palladium as the only precious metal. As is illustrated below, the belief in the art that the general combination of a "precious" metal and a "refractory" metal provides the lowest magnetic susceptibility is incorrect. Rather, specific combinations of metals in known quantities can provide alloys with ultra-low magnetic susceptibilities. Accordingly, as will be further illustrated below, specific palladium containing alloys may be provided having ultra-low volumetric magnetic susceptibility, which, in certain embodiments, may be between $3\times10^{-6}$ and $-3\times10^{-6}$ (cgs). Moreover, the MR image artifact may be reduced by 40% to 60% or more, relative to pure palladium, when an alloy having an ultra-low magnetic susceptibility is provided.

For many investigators, access to MRI equipment is limited, and thus it is convenient to measure a material's magnetic susceptibility using a bench-top method, and correlating that to MRI compatibility. Magnetic susceptibility ($\chi_v$) is a quantification of the magnetization (M) of a material when placed in a magnetic field (H), such that $\chi_v$=M/H. The basic method involves measuring the physical force experienced by a material when placed in a static magnetic field. This disclosure is consistent with the common procedure in the field of studying MRI compatibility, and magnetic susceptibility of an alloy is used to evaluate relative MRI compatibility.

Not all alloy additions are equally suited for MR applications, and there is no means to predict the magnetic susceptibility of the alloys of interest. That is, as is incorrectly suggested by U.S. Patent Application Publication No. 2008/0195194, filed Feb. 11, 2008, and entitled MRI Compatible, Radiopaque Alloys for use in Medical Devices (the '194 publication), selecting elements for inclusion in an alloy based on the magnetic susceptibility of each element does not provide a method of predicting the magnetic susceptibility of an alloy having a combination of the selected elements. Difficulties imposed by the unpredictability of the magnetic susceptibility of alloys in general are exemplified by FIG. 1 (from J. F. Spencer & M. E. John, "The magnetic susceptibility of some binary alloys", Proceedings of the Royal Society of London. Series A, Containing Papers of a Mathematical and Physical Character, Vol. 115, No. 773 61-72 (1927) incorporated by reference in its entirety). Note: to convert from mass to volume susceptibility, multiply by the density (cgs); to convert from cgs units to SI units multiply by $4\pi$. Additional constraints are imposed by any potential additive's effect on both manufacturability and functionality (e.g. biocompatibility, cost, strength, ductility, radiopacity, etc.). Thus, the difficulty in designing an alloy with ultra-low magnetic susceptibility is that, for a given complex alloy, the magnetic susceptibly may not be simply calculated.

Accordingly, to identify compositions that create an ultra-low magnetic susceptibility alloy a substantial amount of empirical data is required. However, for any existing data, the current understanding of the metallurgical technology does not allow one skilled in the art to reliably extrapolate/interpolate magnetic susceptibility data from a given set of compositions to all other compositions, especially with a change of the base metal. Further, the effectiveness of any given alloying addition will depend on the base metal, and all of the other elements present in the alloy. For a given base composition, some elements will be unacceptable additions, regardless of concentration. However, other elements may only be unacceptable over a specific range of compositions. Therefore, embodiments of the present invention provide for the use of specific elements and combinations for achieving an ultra-low magnetic susceptibility. Ultra-low magnetic susceptibility levels in alloys provide materials compatible with today's higher magnetic field strength equipment.

The various embodiments provide palladium-aluminum, palladium-tantalum and palladium-tin based alloys and/or devices, which have small MRI artifacts, and ultra-low magnetic susceptibilities, making the material and/or device compatible with high magnetic field MRI equipment. The embodiments provide synergies discovered when specific elements are added to these palladium (Pd) binary systems. These synergies allow for the optimization of MRI compatibility, manufacturability, biocompatibility, and other design parameters. The characteristics of the alloys provided herein illustrate the advantages of using the inventive alloys over current, commercial, noble-metal alloys.

The palladium-aluminum, palladium-tantalum and palladium-tin based alloys provided herein may further include one or more elemental additions that facilitate providing desirable properties for manufacturability and application. Elemental additions may include: aluminum (Al), tin (Sn), niobium (Nb), tantalum (Ta), tungsten (W), molybdenum (Mo), zirconium (Zr), and titanium (Ti). The combination of the above elements, in specific proportional ranges, allows one skilled in the art to tailor properties such as MRI compatibility, formability, ductility, radiopacity, and strength. In particular, the palladium-tin, palladium-tantalum and palladium-aluminum alloys provided herein exhibit ultra-low magnetic susceptibilities (e.g., between $3\times10^{-6}$ and $-3\times10^{-6}$ cgs units), which are lower than commercially available precious metal alloys. In addition to ultra-low paramagnetic susceptibility alloys, the formulation of diamagnetic palladium based alloys is also provided. The example embodiments provide nominal chemistries. It will be understood by those of skill in the art, that metal alloys have variations in chemistry, including impurities (metallic and otherwise), introduced during material extraction, melting, and processing in general. For example, iron (Fe), cobalt (Co), and nickel (Ni) may have an undesired impact on magnetic susceptibility; arsenic, cadmium, and lead may have an undesired impact on biocompatibility. In order to maintain the material properties, in general, impurities should not total more than 1 at %, and are frequently controlled on the order of 10 ppm and lower. Note that all compositions, unless otherwise noted, are expressed in atomic percent (at %). The use of atomic percent is more relevant than weight percent (wt %) when discussing the impact of elemental concentration on some of the properties discussed herein.

Magnetic Susceptibility

The embodiments provided illustrate how palladium (at least approximately 75 at %) may be alloyed with combinations of Al, Sn, Nb, Ta, W, Mo, Zr, and Ti, in order to improve palladium's MRI compatibility. These elements, when combined to total between 3-25 at % of the palladium alloy, can reduce the magnetic susceptibility, of said alloy, by approximately 80% or greater, and the MR image artifact by approximately 40% or greater. Certain compositions of the above alloy additions may result in an alloy in which the magnetic susceptibility reduction is approximately 95% or greater, and the MR image artifact reduction may be approximately 60% or greater, relative to pure palladium.

Figure 2:
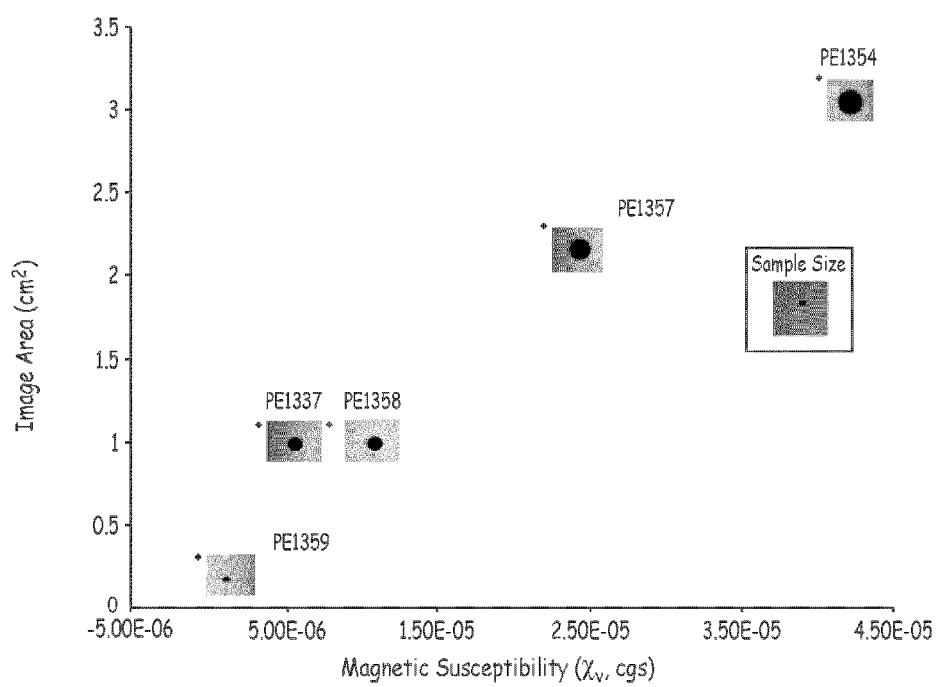
FIG. 2 depicts a graph of magnetic resonance image area versus volumetric magnetic susceptibility for Pd—Al alloys.

Magnetic susceptibility generally correlates to MR image artifact size, the larger the magnetic susceptibility, the larger the artifact. Support may be found in A. A. Zwarun et al., "Relationship of magnetic moment of metallic alloys to image artifact during magnetic resonance imaging", 1650 SPIE Medical Lasers and Systems 33-37 (1992), which is incorporated by reference in its entirety. FIG. 2 is a graph of magnetic susceptibility versus MR image size, including the corresponding MR image for each data point. The graph's inset shows a schematic of the sample cross section, on the same length scale as the MR images. The samples were cylinders oriented perpendicular to Bo. The graph illustrates the trend of decreasing MR image artifact (i.e. how much larger the image is than the actual sample size) with decreasing magnetic susceptibility, using palladium-aluminum binary alloys. However, the trend is a general one, because other variables may impact the image artifact. For a given magnetic susceptibility, two different alloys may not have the same image artifact.

In addition, magnetic susceptibilities for some alloys are not predictable as evidenced by FIG. 1. In some instances, the combinations of additions will completely change the magnetic character of the alloy from paramagnetic (positive magnetic susceptibility), to diamagnetic (negative magnetic susceptibility). The change of a material from paramagnetic behavior to diamagnetic behavior is special, the magnetic moment experienced by a diamagnetic field is perpendicular to the primary magnetic field, compared to parallel for a paramagnetic material. Additionally, providing palladium alloys with negative magnetic susceptibilities, according to certain embodiments, allows more options for MR image control. For instance, the general diamagnetic behavior of the alloy may be matched with the human body.

Alloy Chemistry

According to certain embodiments, in order to achieve an ultra-low magnetic susceptibility for a palladium based alloy, additions of Al, Sn, Nb, Ta, W, Mo, Zr, and Ti, totaling between 3-25 at % may be provided. Some combinations of said elements provide magnetic susceptibilities on the order of $1\times10^{-7}$, while others provide negative magnetic susceptibilities, and some have magnetic susceptibilities below $3\times10^{-6}$. However, not all combinations of the aforementioned additions with palladium provide ultra-low magnetic susceptibilities and specific combinations are required in order to optimize the magnetic susceptibility. In general, desirable combinations of properties are achieved with palladium-tin, palladium-tantalum and palladium-aluminum alloys with additions of Al, Sn, Nb, Ta, W, Mo, Zr, and Ti, added to get additional changes in magnetic susceptibility, as well as other properties, such as formability, and radiopacity.

It is frequently not obvious what additions impact a given property in the desired fashion. It is also not obvious the magnitude of a certain additions impact. Many additives in the prior art recommended for MRI compatible alloys are not acceptable for reducing the magnetic susceptibility of palladium to the levels discussed herein. Examples of elements from the prior art not highly functional for achieving ultra-low magnetic susceptibilities in the concentration levels desired here (no more than 25 at % total additions) are: Re, Ru, Ag, Ir, Ni, Fe, and Co (see, e.g., the '108 and '850, and '120 publications and the '757 patent).

To illustrate, the '194 publication and the '757 patent disclose that in order to lower or maintain the magnetic susceptibility of an alloy, the elements added to the base metal should be of low magnetic susceptibility. That teaching alone does not allow one to design an alloy that has ultra-low magnetic susceptibility. For example, the magnetic susceptibility of the pure elements palladium, tin, aluminum, and silver, are not necessarily an indication of the magnetic susceptibility of an alloy made of some combination of those elements. Palladium has a positive magnetic susceptibility, of $6.1\times10^{-5}$. Tin and aluminum also have positive susceptibilities of $1.8\times10^{-7}$, and $1.7\times10^{-6}$, respectively, while silver has a negative magnetic susceptibility of $-1.9\times10^{-6}$ (Table 1). When 10% of tin, aluminum or silver are added to pure palladium, the susceptibility of all three alloys are similar, and do not correspond to the susceptibilities of the pure elements (i.e. do not follow a rule of mixtures). The susceptibilities are: Pd-10Sn, $1.5\times10^{-5}$; Pd-10Al, $2.2\times10^{-5}$; and Pd-10Ag, $4.0\times10^{-5}$ (Table 1). This counter intuitive behavior of magnetic susceptibility may be further expanded to ternary alloys.

As the number of elements in an alloy increases, the complexity of interactions increases. In some instances, in light of the binary alloy data above, the interaction may provide an unexpected change in magnetic susceptibility.

According to embodiments of the present invention, it has been discovered that in a palladium-aluminum alloy system, a ternary addition of tin has a dramatic synergy, compared to a ternary addition of silver. A Pd-10Al-10Ag alloy has a magnetic susceptibility similar to the 10% binary alloys ($1.1 \times 10^{-5}$), whereas the Pd-10Al-10Sn alloy, of the present invention, has a magnetic susceptibility, of $-1.0 \times 10^{-6}$, which is diamagnetic and a full order or magnitude lower (Table 1). As illustrated by the discussion above, and as provided in Table 1, the resulting ultra-low magnetic susceptibility Pd-10Al-10Sn alloy of the present invention is not expected in view of the prior art. Additional palladium-aluminum ternary alloys having an ultra-low magnetic susceptibility include those that include aluminum at 5% and 10% with additions of 10% tantalum (Table 1).

TABLE 1

| Alloy (at %) | Alloy Code | Magnetic Susceptibility |
|---|---|---|
| Pd (100%) | 924 | $7.6 \times 10^{-5}$ |
|  | Lit value* | $6.1 \times 10^{-5}$ |
| Sn ("white") | Lit. Value** | $1.8 \times 10^{-7}$ |
| Al (100%) | Lit. Value* | $1.7 \times 10^{-6}$ |
| Ag (100%) | 1345 | $-2.4 \times 10^{-6}$ |
|  | Lit. Value* | $-1.9 \times 10^{-6}$ |
| Pd—10Sn | 1403 | $1.5 \times 10^{-5}$ |
| Pd—10Al | 1357 | $2.2 \times 10^{-5}$ |
| Pd—10Ag | Lit. Value*** | $4.0 \times 10^{-5}$ |
| Pd—10Al—10Ag | 1385 | $1.1 \times 10^{-5}$ |
| Pd—10Al—10Sn | 1377 | $-1.0 \times 10^{-6}$ |
| Pd—5Al—10Ta | 1365 | $2.0 \times 10^{-6}$ |
| Pd—10Al—10Ta | 1371 | $-3.9 \times 10^{-7}$ |
| Pd—5Al—5Sn—5Ta | 1417 | $3.7 \times 10^{-7}$ |

*Handbook of Chemistry and Physics, 1st Student Edition, Weast, CRC Press, 1988
**Honda, et al., "Paramagnetic and Diamagnetic Data," International Critical Tables Volume VI, 1st Edition, McGraw-Hill, 1929
***Budworth, et al. "The termal and magnetic properties of some The discovered synergistic response of the present invention is not isolated to the palladium-aluminum system. Additional embodiments of the present invention provide a palladium-tin alloy system with ternary alloy additions, which result in alloys having ultra-low magnetic susceptibilities. Table 2 provides, in part, a listing of palladium-tin ternary alloys having ultra-low magnetic susceptibilities. As can be seen, each of the ternary additions of Ta, Al, Mo, Nb and W provide alloys having an ultra-low magnetic susceptibility.

TABLE 2

| Alloy (at %) | Alloy Code | Magnetic Susceptibility |
|---|---|---|
| Pd—10Sn—5Ta | 1391 | $4.7 \times 10^{-7}$ |
| Pd—10Sn—10Al | 1377 | $-1.0 \times 10^{-6}$ |
| Pd—10Sn—5Mo | 1424 | $2.83 \times 10^{-7}$ |
| Pd—10Sn—5Nb | 1423 | $3.00 \times 10^{-7}$ |
| Pd—10Sn—5W | 1422 | $7.27 \times 10^{-7}$ |

However, as with other alloy systems, the magnetic susceptibility of palladium-tin ternary alloys is unpredictable, and not all ternary additions to a palladium-tin alloy system result in an ultra-low magnetic susceptibility alloy. For example, as illustrated in Table 3, in the palladium-tin system, a ternary alloy addition of tantalum having a magnetic susceptibility $1.41 \times 10^{-5}$, is compared to that of rhenium having a magnetic susceptibility of $7.55 \times 10^{-6}$. Although tantalum has a higher magnetic susceptibility than rhenium, the palladium-tin alloy with tantalum, Pd-10Sn-5Ta, has a magnetic susceptibility ($4.7 \times 10^{-7}$) that is an order of magnitude less than the alloy with rhenium, Pd-10Sn-5Re ($6.86 \times 10^{-6}$).

TABLE 3

| Alloy (at %) | Alloy Code | Magnetic Susceptibility |
|---|---|---|
| Ta (100%) | Lit. Value* | $1.41 \times 10^{-5}$ |
| Re (100%) | Lit. Value* | $7.55 \times 10^{-6}$ |
| Pd—10Sn—5Ta | 1391 | $4.7 \times 10^{-7}$ |
| Pd—10Sn—5Re | 1421 | $6.86 \times 10^{-6}$ |

*Handbook of Chemistry and Physics, 1st Student Edition, Weast, CRC Press, 1988

While certain embodiments of the invention provide ultra-low magnetic susceptibility ternary alloys, other quaternary or higher order alloys having ultra-low magnetic susceptibilities may be provided for alloys having at least 75 at % palladium. Table 4 contrasts a binary and ternary alloy to a quaternary alloy, using a palladium-tantalum basis, which also shows the special ability to provide ultra-low magnetic susceptibilities. A binary Pd-15Ta alloy (1361) has a susceptibility of $-4.4 \times 10^7$. By replacing 10% of the Ta with 5% Nb and 5% V (alloy 1446), the susceptibility rises to level outside of the desired ultra-low characteristic (Table 4). However, by substituting 2.5% Zr and 2.5% Ti for the 5% V (alloy 1447), the magnetic susceptibility is, again in the $10^{-7}$ range. For the palladium-tantalum system, rhenium and vanadium do not provide the desired magnetic susceptibility characteristics, whereas zirconium and titanium do. For achieving ultra-low magnetic susceptibilities, tungsten behaves in a similar manner to niobium.

TABLE 4

| Alloy (at %) | Alloy Code | Magnetic Susceptibility |
|---|---|---|
| W (100%) | Lit. Value* | $5.6 \times 10^{-6}$ |
| Re (100%) | Lit. Value* | $7.6 \times 10^{-6}$ |
| Ta (100%) | Lit. Value* | $1.4 \times 10^{-5}$ |
| Nb (100%) | Lit. Value* | $1.9 \times 10^{-5}$ |
| Mo (100%) | Lit. Value* | $7.7 \times 10^{-6}$ |
| Pd—15Ta | 1361 | $-4.4 \times 10^{-7}$ |
| Pd—15W | 1490 | $7.3 \times 10^{-6}$ |
| Pd—15Re | 1516 | $1.2 \times 10^{-5}$ |
| Pd—6.5Ta—7.6Re | 1401 | $7.9 \times 10^{-6}$ |
| Pd—7.5Ta—7.5W | 1470 | $1.7 \times 10^{-6}$ |
| Pd—5Ta—5Nb—5V | 1446 | $4.6 \times 10^{-6}$ |
| Pd—5Ta—5Nb—2.5Ti—2.5Zr | 1447 | $6.8 \times 10^{-7}$ |

Frequently, metallurgical teachings seek to categorize elemental effects in an alloy, by a general element type, such as "platinum group metals," or "refractory metals." Just as a pure element's magnetic susceptibility does not indicate that element's impact on the magnetic susceptibility of an alloy, neither does the element's "group." This can be illustrated with both binary and ternary alloys. The magnetic susceptibilities of refractory metals W, Re, Ta, Nb, and Mo are listed in Table 4. When a binary Pd plus refractory metal alloy is considered, Pd-15Re and Pd-15W, both have susceptibilities above $3 \times 10^{-6}$, while Pd-15Ta is well below that (Table 4). Further, a ternary alloy, Pd-6.5Ta-7.9Re, is above $3 \times 10^{-6}$, but Pd-7.5Ta-7.5 W is well below. Thus, in contrast to the teachings of the '850 and '108 publications, in the present invention, the general combination of precious metals and refractory metals, does not apply.

Further, additives such as rhenium and tantalum may have a different synergistic effect on the magnetic susceptibility of a palladium-aluminum ternary alloy, in comparison to the effect they have as a binary addition to pure Pd. An alloy of 5% Al, 9% Ta and the balance palladium has a magnetic susceptibility of $1.73 \times 10^{-6}$, while an alloy of 5% Al, 9% Re and the balance palladium has a magnetic susceptibility of $1.34 \times 10^{-5}$. In the Pd—Al system, Ta has a greater effect than Re on lowering the magnetic susceptibility.

It has been found, in particular, that palladium-tin, palladium-tantalum, and palladium-aluminum alloys, with additions of Al, Sn, Nb, Ta, W, Mo, Zr, and Ti, are particularly suited to producing an ultra-low magnetic susceptibility alloy, when total additions, to palladium, total up to 25%. Some combinations of these elements produce diamagnetic alloys, as illustrated in Tables 1 and 2, including Pd-10Al-10Sn, Pd-10Al-10Ta and Pd-10Sn-10Al.

Figure 3:
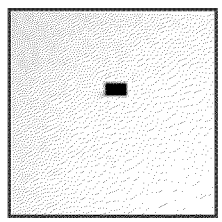
FIG. 3 depicts a comparison of MR images of Pt-8 wt % W, and Pd-25 at % Al.
Figure 3:
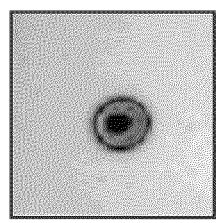
Figure 3:
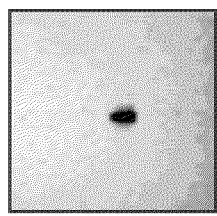

The above lessons on the reduction of magnetic susceptibility may be applied to improve MRI compatibility. Surprisingly, it has been found that the disclosed embodiments exhibit a significant decrease in MR image area compared to any noble metal based medical alloy system in commercial use. For example, FIG. 3 illustrates a reduction in image artifact possible through the use of this disclosure. Considering the improved MRI characteristics and the cost savings of Pd-alloys over Pt-alloys, any of the Pd-alloys, having the above mentioned chemistries, with an ultra-low magnetic susceptibility, is an improvement over the prior art.

Properties of Ultra-Low Magnetic Susceptibility Alloys

Formability and Mechanical Properties: The alloys provided according to certain embodiments satisfy a number of varied properties beyond a small MRI artifact and low magnetic susceptibility. Table 5 provides various biomedical applications, listing the relative importance of MRI compatibility, strength, and biocompatibility.

TABLE 5

| Application | MRI Characteristics: Importance of | | | | Strength: Importance | | Biocompatability: Importance | |
|---|---|---|---|---|---|---|---|---|
| | force | heat | artifact | Reason | | Reason | | Reason |
| Guide wires | high | low | medium | temp item but needs to be manipulated | high | prevent permanent kinks | medium | acute only; but need to avoid leaving debris |
| leadwires Neuro | high | high | med | chronic- low perfusion, adjacent to small structures | medium | fatigue, body movement forces | medium | inside insulating urethane for silicone |
| neuro-stimulation electrodes | high | high | high | touching sensitive tissue, low perfusion, electrode easily dislodged | low | only needed to maintain position | high | chronic intrathecal implant |
| orthopedic screws | low | medium | high | High- adjacent to tissue char change could cause false Dx | high | torque | high | chronic implant; some screws are removed after healing |
| ablation tips | high | low | high | may need to be maneuvered during MRI, no need to worry about heat, need high resolution to position for ablation | low | high mass, machined, no mechanical load in use | low | only acute toxicity |
| Cannula | high | high | high | position during MRI, guides other item, must not distort Dx | high | thin walled tube, needs to maintain sharp edge | medium | usually acute only |
| leadwires CRM | med | low | low | well anchored by tissue, no touch tissue, in veins | medium | short lengths, supported by tissue, stressed by movement | | |
| CRM electrodes | med | high | low | well perfused, tightly anchored in chronic phase | design related | pigtails need high strength, others not as much | | |
| shock coils | low | low | low | high energy, necrotic tissue unimportant, effects are pan-ventricular | low | not much mechanical stress | high | chronic implant |
| feed through leads | low | low | low | internal to device | low | annealed during sealing operation | low | |
| implantable connectors | med | low | low | | high | small size - higher gram force desirable | low | no touch tissue |
| marker coils/bands | low | high | low | heat in intimal layer of artery is risk | low | no mechanical load, needs to be ductile for crimping | high | chronic implant |
| stents | low | high | low | | high | resist lateral force | high | chronic implant |
| embolic coils | high | med | low | translational or rotational force might "organize" coils to be ineffective | high | stop blood flow, position retention | high | chronic implant |

TABLE 5-continued

| Application | MRI Characteristics: Importance of | | | | Strength: Importance | | Biocompatability: Importance | |
|---|---|---|---|---|---|---|---|---|
| | force | heat | artifact | Reason | | Reason | | Reason |
| surgical tools | high | low | low | dangerous flying objects with sharp edges | design dependent | depending on use - in general higher strength won't hurt | low | only acute toxicity |
| enclosures/ housings | high | | low | | design | | high | chonic implant |
| vena cava filters | high | low | low | big, but with high perfusion | high | used in high blood flow location | very high | erthrycytes flow through |
| sutures & staples & clips | high | high | low | must not move in large static field, rips tissue | high | retain shape and closure | high | chronic, |
| Catheter components-invasive | high | low | low | acute only, usually in good flow | medium | | medium | temporary |
| Catheter comp - non-invasive | high | high | low | Foley catheter, | medium | | low | not inside body |

Another example of an important combination of properties would be MRI compatibility, strength, and formability. Maximizing properties such as strength and formability is typically difficult because the controlling mechanisms compete, and generally, the higher a material's strength, the lower the formability of the material, and vice versa.

According to certain embodiments, novel combinations of metals results in MRI compatibility, good hardness, and good formability is the differences observed between alloys in the family of Pd—Sn, Pd—Al, and Pd—Ta alloys. For instance, both Pd-25Al (Alloy 1359), and Pd-15Ta (Alloy 1361) are MRI compatible, with magnetic susceptibilities of −7.0E-7, and −4.4E-7 respectively. They both have limited cold formability and good hardness. Conversely, ternary alloys of the present invention of Pd-10Al-10Sn and Pd-5Ta-10Sn, have MRI compatibility, an ultra-low magnetic susceptibility, good hardness, and cold formability. Table 6 lists these alloys, and their magnetic susceptibilities and mechanical properties including hardness, and formability to illustrate novel composition-property relationships. Max formability is taken as the percent cold work done to the as-cast material before excessive cracking is observed. In moving from Pd-25Al and Pd-15Ta, to Pd-10Al-10Sn and Pd-10Sn-5Ta, the magnetic susceptibility remained low, the strength remained acceptable, and the formability was surprisingly improved.

application. That said, general screening tests can be performed to determine if an alloy may be more or less appropriate for a type of application. There are some elements that are almost universally avoided in medical applications, due to their poisonous nature. These are lead, arsenic, and cadmium.

Medical Devices Formed of Ultra-Low Magnetic Susceptibility Alloys

Each of the alloy additives/composition ranges provided in the embodiments exhibits a reduction in magnetic susceptibility and MRI image area compared to palladium alone. Additives of Al, Sn, Nb, Ta, W, Mo, Zr, and Ti used in palladium-based alloys alter the magnetic characteristics and electrical properties of palladium, making the alloy better suited for MRI purposes, and are biocompatible. Accordingly, medical devices fabricated from the palladium-based alloys of the aforementioned embodiments, and variants thereof, are suitable for contact with portions of the body where MR procedures are commonly performed. When such palladium-based alloys are used as or in a medical device or aid, the MRI artifact associated with the alloy may thus be comparatively small making the resulting MRI suitable for analysis, treatment, diagnostic, and procedural purposes. Medical devices and aids containing a palladium-based alloy contemplated include may be electrically active or electrically passive, and may include, but are not limited to: stents,

TABLE 6

| Alloy (at %) | Alloy Code | Magnetic Susceptibility (volume, cgs units) | Hardness (As-Cast) | Hardness (cold worked) | Max Cold Work "Formability" |
|---|---|---|---|---|---|
| Pd—25Al | 1359 | $-7.0 \times 10^{-7}$ | 520 | N/A | <20% |
| Pd—15Ta | 1361 | $-4.4 \times 10^{-7}$ | 275 | N/A | <20% |
| Pd—10Sn—10Al | 1377 | $-1.0 \times 10^{-6}$ | 300 | 480 | 75% |
| Pd—10Sn—5Ta | 1391 | $4.7 \times 10^{-7}$ | 240 | 440 | 75% |
| Pd—5Al—10Ta | 1365 | $2.0 \times 10^{-6}$ | 270 | 400 | 75% |
| Pd—10Al—10Ta | 1371 | $-3.9 \times 10^{-7}$ | 455 | 550 | <20% |

Figure 4:
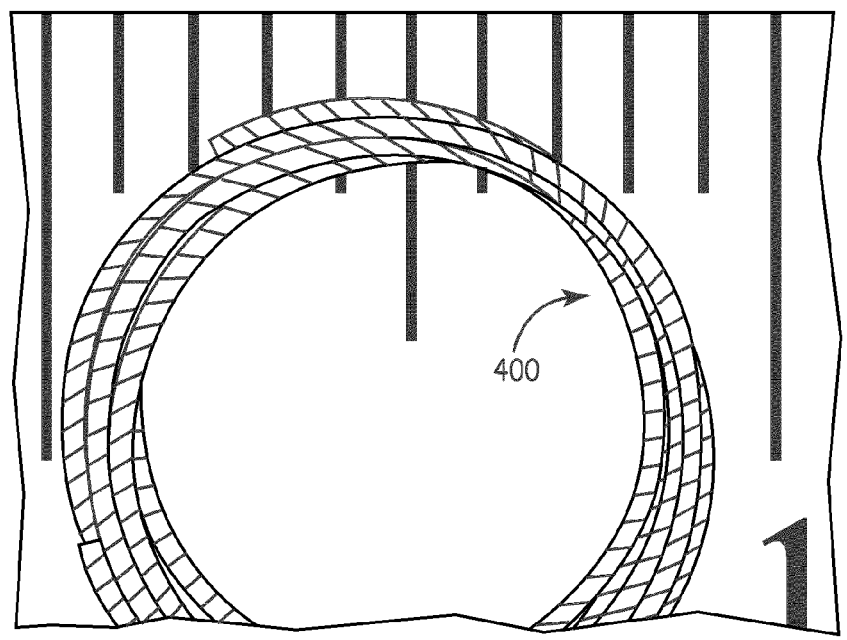
FIG. 4 is an image of an embolic coil, in which all or a portion of the embolic coil may be formed of a palladium-based alloy having an ultra-low magnetic susceptibility according, to embodiments of the invention.
Figure 5:
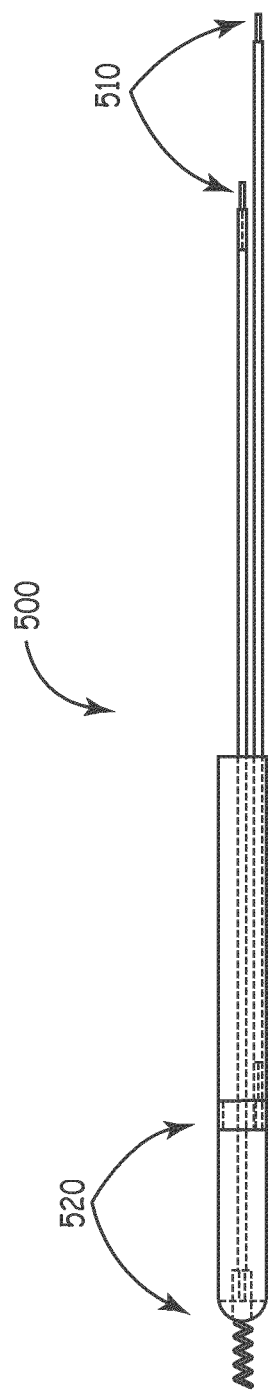
FIG. 5 provides an example of a lead that includes lead wires and electrodes, each of which may be formed of a palladium-based alloy having an ultra-low magnetic susceptibility, according to embodiments of the invention.

Biocompatibility: The biocompatibility of any alloy used in a medical environment is critical. The required level of biocompatibility is predicated on the use of the alloy. Table 5 above provides examples of various medical devices, with a rating of the required level of biocompatibility. The biocompatibility of an alloy needs to be evaluated for the specific guide wires, needles, embolism coils, electrodes, electrical contacts, markers, filters, ablation coils, rods, plates, clips, and staples. FIGS. 4-5 depict medical devices and aids in which all or a portion of the medical device or aid may be formed of a palladium-based alloy. FIG. 4 is an image of an embolic coil 400, a type of electrically passive medical device, in which all or a portion of the embolic coil may be formed of the presently described palladium-based alloys having an ultra-low magnetic susceptibility. FIG. 5 provides an example of a lead 500, a type of electrically active medical device, which includes lead wires 510 and electrodes 520, each of which may be formed of a palladium-based alloy having an ultra-low magnetic susceptibility, according to embodiments of the invention.

The devices contemplated may have all or a portion of the composition as a palladium-based alloy. Such devices are particularly suited for use inside the human body, e.g., where MRI imaging is performed, and may include all applications outside of dentistry. Because of constraints related to casting temperature and thermal expansion characteristics for dental porcelain fused to metal (PFM) and crown and bridge (C&B) alloys, dental alloys are outside the scope of this invention. Implements within the scope of this work may be manufactured from cast, wrought, powder, liquid (e.g. physical vapor deposition), or gaseous material (e.g. physical or chemical vapor deposition) as a finished product/component, or formed/machined/fabricated into a finished product/component.

Embodiments of the invention may be fabricated via a number of methods. The inventive alloys may be formed through typical processes, as known to those skilled in the art, such as: casting, powder metallurgy, reaction synthesis, diffusion coupling, physical vapor deposition, chemical vapor deposition, or any comparable process. The primary method of forming the alloy may also serve as a method of providing a finished product. Additionally, after creating the alloy, it may be further processed by one skilled in the art into a finished product/component, for example: wrought, forged, hot pressed, hot isostatic pressed, swaged, extruded, drawn, machined, heat treated, formed, stamped, or welded.

Testing Techniques

The magnetic susceptibility measurements presented herein are volumetric magnetic susceptibility measurements based on centimeters grams seconds (cgs) units. A Johnson Matthey Auto Magnetic Susceptibility Balance ("MSB-Auto"), manufactured by Sherwood Scientific Limited of Cambridge England, was used at ambient temperature to measure the volumetric magnetic susceptibility. Samples of pure palladium and silver were used as comparison standards. The MSB-Auto uses a 4.5 k Gauss magnetic field, and has a reported measurement range from $0.001 \times 10^{-7}$ to $1.99 \times 10^{-4}$ (volumetric susceptibility, cgs units). The MSB-Auto measures cylindrical samples, 4.17 mm or 3.05 mm in diameter and 45.7 mm long. The relative physical force exerted on a material in a magnetic field, such as in MRI, may be inferred by measurements taken by the MSB-Auto. As the magnetic susceptibility approaches zero, the physical force will approach zero. For a given magnetic susceptibility, the magnitude of the induced magnetic force will scale with the magnetic field strength. As with the magnetic force, a general trend between the reduction of magnetic susceptibility and MRI image artifact, has been established empirically.

MR images reported in this application were performed on a Siemens Trio MR scanner with a 3.0 Tesla primary magnetic field ($B_0$). The MRI parameters were 190×190 mm field of view, 4 mm slice thickness, 260 Hz/pixel bandwidth, 256×256 pixel matrix, 90° flip angle, and a TR/TE ratio of 900/2.77 ms. Images were taken through the samples center of mass. Samples were set in a "phantom" (agar filled container), 17.8 cm long×14.0 cm wide and 8.9 cm thick. Samples were arranged in a matrix such that MR image artifacts did not overlap the edge of the phantom, and did not overlap the adjacent artifacts. Samples in the form of cylinders, hemispherical discs, straight wire, and coiled wire were imaged. The samples were imaged with their "axis" both parallel, and perpendicular to the primary magnetic field.

The images were then analyzed to determine the extent of image ghosting. One way to quantify the image artifact is to take the difference between the actual samples geometry/dimensions and those of the image. Another way to quantify the image artifact is to make a relative comparison between the ghosts produced by different samples. Generally, depending on sample geometries, and materials used, the MRI artifact size changes when the physical orientation of the sample changes relative to the magnetic fields. The same dependence applies to the orientation of the imaging plane, and the imaging parameters used. Any variations due to imaging and sample orientation should be considered when evaluating MRI data. Within comparisons made, in this disclosure, an effort was made to keep the extrinsic variables (i.e. sample orientation, magnetic field strength, etc.) constant.

From the above description and drawings, it will be understood by those of ordinary skill in the art that the particular embodiments shown and described are for purposes of illustration only and are not intended to limit the scope of the present invention. Those of ordinary skill in the art will recognize that the present invention may be embodied in other specific forms without departing from its spirit or essential characteristics. References to details of particular embodiments are not intended to limit the scope of the invention.

What is claimed is:

1. A palladium-tin ternary or higher alloy consisting of:
   a. at least 75 at % palladium;
   b. between about 5 and 20 at % tin; and
   c. one or more additives chosen from: aluminum, tantalum, niobium, tungsten, molybdenum, and titanium, in an amount of at least 5 at % total and up to about 20 at % total, wherein the palladium-tin ternary or higher alloy has an ultra-low magnetic susceptibility with a volumetric magnetic susceptibility at or below 3×10-6 (cgs), and wherein the palladium-tin alloy is biocompatible.

2. The alloy of claim 1, wherein the one or more additives is up to 10 at % total.

3. The alloy of claim 1, wherein the alloy forms at least a portion of a medical device.

4. The alloy of claim 3, wherein the medical device comprises an electrically active medical device.

5. A palladium-aluminum ternary or higher alloy, consisting of:
   a. at least 75 at % palladium;
   b. between 5 and 20 at % aluminum; and
   c. one or more additives chosen from: tin, tantalum, or titanium, up to 20 at % total, wherein the palladium-aluminum ternary or higher alloy has an ultra-low magnetic susceptibility with a volumetric magnetic susceptibility at or below 3×10-6 (cgs) and is biocompatible.

6. The alloy of claim 5, wherein the one or more additives is up to 10 at % total.

7. The alloy of claim 5, wherein the alloy forms at least a portion of a medical device.

8. The alloy of claim 7, wherein the medical device comprises an electrically active medical device.

9. A palladium-tantalum ternary or higher alloy, consisting of:
   a. at least 75 at % palladium;
   b. between 10 and 20 at % tantalum; and
   c. a balance of the palladium-tantalum ternary or higher alloy including one or more additives chosen from: tin, aluminum or niobium wherein the palladium-tantalum ternary or higher alloy has an ultra-low magnetic susceptibility with a volumetric magnetic susceptibility at or below 3×10-6 (cgs) and is biocompatible.

10. The alloy of claim 9, wherein the one or more additives is up to 10 at % total.

11. The alloy of claim 9, wherein the alloy forms at least a portion of a medical device.

12. The alloy of claim 11, wherein the medical device comprises an electrically active medical device.

13. A palladium alloy, consisting of:
 a. at least 75 at % palladium;
 b. a minimum of 5 at % aluminum;
 c. a minimum of 5 at % tin; and
 d. a minimum of 5 at % tantalum,
  wherein the palladium alloy has an ultra-low magnetic susceptibility with a volumetric magnetic susceptibility at or below 3×10-6 (cgs), and wherein the palladium alloy is biocompatible.

14. The alloy of claim 13, wherein the alloying additions are up to 15 at % total.

15. The alloy of claim 13, wherein the alloy forms at least a portion of a medical device.

16. The alloy of claim 15, wherein the medical device comprises an electrically active medical device.

17. An electrically active medical device, consisting of:
 a palladium ternary or higher alloy comprising:
  at least 75 at % palladium; and
  two to four additions of tin, aluminum, tantalum, niobium, tungsten, molybdenum, zirconium and titanium totaling between about 15 and 25 at %, wherein at least one of the additions includes tin, aluminum or tantalum, and
 wherein the portion of the electrically active medical device formed of the palladium ternary or higher alloy has an ultra-low magnetic susceptibility with a volumetric magnetic susceptibility at or below 3×10-6 (cgs) and is biocompatible.

18. The medical device of 17, wherein the electrically active medical device comprises one or more of: a neuro-stimulation electrode, a cardiac pacing electrode, and a cardiac defibrillation shock coil.

19. An electrically passive medical device, consisting of:
 a palladium ternary or higher alloy comprising:
  at least 75 at % palladium; and
  two to four additions of tin, aluminum, tantalum, niobium, tungsten, molybdenum, zirconium and titanium totaling between about 15 and 25 at %, wherein at least one of the additions includes tin, aluminum or tantalum in an amount of at least 2.5 at % total, and
 wherein the portion of the electrically passive medical device formed of the palladium ternary or higher alloy has an ultra-low magnetic susceptibility with a volumetric magnetic susceptibility at or below 3×10-6 (cgs) and is biocompatible.

20. The medical device of 19, wherein the electrically passive medical device comprises one or more of: an embolic coil, a guide wire, a vena cava filter, a suture, a staple, and a clip.

21. The alloy of claim 3, wherein the medical device comprises an electrically passive medical device.

22. The alloy of claim 7, wherein the medical device comprises an electrically passive medical device.

23. The alloy of claim 11, wherein the medical device comprises an electrically passive medical device.

24. The alloy of claim 4, wherein the electrically active medical device comprises one or more of: a neuro-stimulation electrode, a cardiac pacing electrode, and a cardiac defibrillation shock coil.

25. The alloy of claim 8, wherein the electrically active medical device comprises one or more of: a neuro-stimulation electrode, a cardiac pacing electrode, and a cardiac defibrillation shock coil.

26. The alloy of claim 12, wherein the electrically active medical device comprises one or more of: a neuro-stimulation electrode, a cardiac pacing electrode, and a cardiac defibrillation shock coil.

* * * * *

UNITED STATES PATENT AND TRADEMARK OFFICE
CERTIFICATE OF CORRECTION

Page 1 of 1

PATENT NO.      : 9,234,262 B2
APPLICATION NO. : 12/358629
DATED           : January 12, 2016
INVENTOR(S)     : Arthur S. Klein et al.

It is certified that error appears in the above-identified patent and that said Letters Patent is hereby corrected as shown below:

SPECIFICATION

| Column | Line | PTO | Should Be |
|---|---|---|---|
| 5 | 30 | "order of 10 ppm and" | -- order of 100 ppm and -- |
| 5 | 60 | "perpendicular to Bo." | -- perpendicular to $B_0$. -- |
| 8 | 18 | "$-4.4 \times 10^7$." | -- $-4.4 \times 10^{-7}$. -- |

Signed and Sealed this
Tenth Day of May, 2016

Michelle K. Lee
*Director of the United States Patent and Trademark Office*